United States Patent [19]

Sakashita et al.

[11] Patent Number: 5,455,174
[45] Date of Patent: Oct. 3, 1995

[54] PROCESS FOR THE STEREOSELECTIVE ESTERIFICATION OF ASCORBIC OR ERYTHORBIC ACIDS WITH LONG-CHAINED ENOL ESTERS

[75] Inventors: Keiichi Sakashita; Shiro Miyamoto; Akihiro Sakimae, all of Otake, Japan

[73] Assignee: Mitsubishi Rayon Company, Ltd., Tokyo, Japan

[21] Appl. No.: 117,360

[22] Filed: Sep. 7, 1993

Related U.S. Application Data

[63] Continuation of Ser. No. 881,208, May 11, 1992, abandoned.

[30] Foreign Application Priority Data

May 18, 1991 [JP] Japan ................................. 3-113591
Sep. 14, 1991 [JP] Japan ................................. 3-262943
Nov. 6, 1991 [JP] Japan ................................. 3-289958

[51] Int. Cl.⁶ .................................................. C12P 41/00
[52] U.S. Cl. ........................ 435/280; 435/126; 435/176; 435/177
[58] Field of Search ............................ 435/280, 126, 435/135, 176, 177, 183

[56] References Cited

U.S. PATENT DOCUMENTS

| | | | |
|---|---|---|---|
| 3,770,588 | 11/1973 | Forgione | 195/63 |
| 4,525,457 | 6/1985 | Sakata et al. | 435/178 |
| 4,873,194 | 10/1989 | Sawamura et al. | 435/198 |
| 5,079,153 | 1/1992 | Enomoto et al. | 435/126 |

FOREIGN PATENT DOCUMENTS

| | | |
|---|---|---|
| 321918 | 6/1989 | European Pat. Off. . |
| 337920 | 10/1989 | European Pat. Off. . |
| 0401704 | 12/1990 | European Pat. Off. . |
| 5488261 | 7/1979 | Japan . |
| 59-170085 | 9/1984 | Japan . |

OTHER PUBLICATIONS

Wang, Y., J. Am. Chem Soc. 110:7200–05 (1988).

Patent Abstracts Of Japan, vol. 16, No. 63, (C–911) [5106], Feb. 18, 1992, & JP–A–3–259089, Nov. 19, 1991, K. Enomoto, et al., "Production Of Organic Acid Ester".

*Primary Examiner*—Marian C. Knode
*Assistant Examiner*—S. Saucier
*Attorney, Agent, or Firm*—Oblon, Spivak, McClelland, Maier & Neustadt

[57] ABSTRACT

An organic acid ester of ascorbic acid or erythorbic acid is produced by reacting ascorbic acid or erythorbic acid with an organic acid enol ester in an organic solvent with a solubility of ascorbic acid or erythorbic acid of more than 0.3% at 25° C. in the presence of an active lipase.

6 Claims, No Drawings

PROCESS FOR THE STEREOSELECTIVE ESTERIFICATION OF ASCORBIC OR ERYTHORBIC ACIDS WITH LONG-CHAINED ENOL ESTERS

This application is a continuation of application Ser. No. 07/881,208, filed on May 11, 1992, now abandoned.

BACKGROUND OF THE INVENTION

1. Field of the Invention

The present invention relates to a process for producing an organic acid ester of ascorbic acid or erythorbic acid by utilizing a transesterification by an enzyme.

2. Discussion of the Background

Ascorbic acid and erythorbic acid are widely used as an additive for foodstuffs and cosmetics to prevent their oxidation, because ascorbic acid and erythorbic acid have a strong reducing ability.

Nevertheless, since ascorbic acid and erythorbic acid can not easily dissolve in oils, they are converted into their organic acid ester with a high oil solubility, such as palmitate, myristate or stearate, to inhibit the oxidation of oily foodstuffs, such as nuts, potato chips, mayonnaise, margarine, fried snacks and so on.

Moreover, some salts of organic acid esters of ascorbic acid are useful as a surface active agent for foodstuffs, and anti-browning agent for fruits and flowers.

A process for preparing ascorbic acid-6-palmitic acid ester has been disclosed in Japanese Patent Application Laid-open No. 54-88261. In this process, hydrogen fluoride is used as a solvent and as a catalyst.

Also, Japanese Patent Application Laid-open No. 59-170085 has disclosed a process for preparing a fatty acid ester of ascorbic acid in which a sulfuric acid having a concentration of higher than 96% is used as a solvent and as a catalyst.

In these processes, a strongly corrosive acid, such as hydrogen fluoride or sulfuric acid, is used. Therefore, the processes have such disadvantages that apparatus and vessels must be highly resistant to corrosion, that the handling of the reaction mixture is difficult, and that a large amount of an alkali is required for the waste water.

To overcome the disadvantages of the conventional processes, a process for the preparation of an ester by reacting ascorbic acid or erythorbic acid with a carboxylic acid or its ester in an organic solvent in the presence of an enzyme as a catalyst has been proposed in Japanese Patent Application No. 27069/1990 (Japanese Patent Application Laid-open No. 3-117495, European Patent-A2 0 401 704) by one of the present inventors and others. This process has an advantage that the reaction can be carried out under milder conditions with high selectivity than those of the conventional processes and that conventional plants may be used. Nevertheless, since the ester synthesis according to this process is essentially equilibrium, the concentration of the ester of ascorbic acid or erythorbic acid in the reaction mixture is only 2 or 3% due to the formation of water. Therefore, the productivity is not satisfactory.

SUMMARY OF THE INVENTION

As a result of continuing research to overcome the defects explained above, it has now been found that an organic acid ester can be synthesized at a high reaction rate and in a high concentration when ascorbic acid or erythorbic acid is reacted with an organic acid enol ester represented by the general formula (I)

wherein $R_1$ denotes an alkyl, aralkyl or aryl group, and $R_2$ denotes hydrogen atom or methyl group, in an organic solvent, whose solubility (wt/vol) of ascorbic acid or erythorbic acid at 25° C. is 0.3% or more, in the presence of an active lipase to form an organic ester of ascorbic acid or erythorbic acid represented by the general formula (II) or (III)

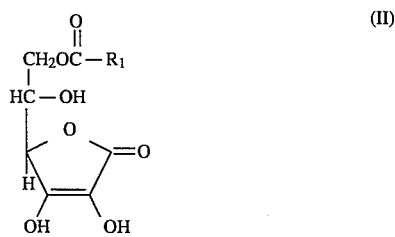

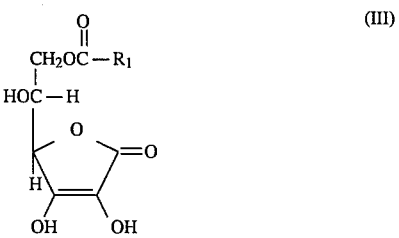

wherein $R_1$ is as defined above.

DETAILED DESCRIPTION OF THE INVENTION

In the present invention, although the number of carbon atoms of the alkyl group denoted by $R_1$ in the general formula is not particularly restricted, the alkyl group includes groups ranging from an alkyl group with comparatively small number of carbon atoms such as methyl group (number of carbon atom=1), ethyl group (number of carbon atoms=2) and propyl group (number of carbon atoms=3) to a longer alkyl group such as dodecyl group (number of carbon atoms=12), pentadecyl group (number of carbon atoms=15) and hexadecyl group (number of carbon atoms=16). The alkyl group also includes those having an unsaturated bond, such as oleyl group. As the aralkyl group there may be mentioned, e.g., benzyl group, and as the aryl group, there may be mentioned, e.g., phenyl group.

As the synthesis of esters, a direct synthesis of an ester from an acid and an alcohol, a transesterification of an ester with an alcohol and a transesterification of an ester with an acid are well known. These are all equilibrium reactions, and thus, it is required to separate such by-products as water, alcohol and acid from the reaction system with a good efficiency to obtain the product with a high conversion. In the preparation of an ester by using an enzyme, the conditions required are all the same.

The reasons why an organic acid enol ester is used as a substrate for producing the ester are as follows:

(1) Such an ester has a low bond energy between the alkoxy moiety and the acyl moiety so that an enzyme-acyl complex is easily formed, and (2) Acetone or acetaldehyde formed as a by-product of the transesterification can not be a substrate for the following transesterification, and thus a reverse reaction will not proceed so that the ester can be prepared at a high conversion.

Various reactions have been carried out for the synthesis of an ester in an organic solvent by using an enzyme. It is said that the logarithmic value (log p) of the partition coefficient (p) of the organic solvent between octanol and water is a yardstick of selecting the organic solvent for such reactions. It has been reported that an organic solvent whose log p is 2 or more, preferably 4 or more, is preferred for carrying out the enzyme reaction stably (C. Laane, J. Tramper and M. D. Lilly, Stud. Org. Chem., 29 65 (1987)).

On the other hand, ascorbic acid or erythorbic acid used in the present invention is highly water soluble and an organic acid enol ester is highly oil soluble. Therefore, the solvent whose log p is 2 or more does not dissolve both the ascorbic acid or erythorbic acid and the enol ester. To solve this problem, a bicomponental system consisting of a solvent with a greater value of log p and water can be taken into consideration. However, since ascorbic acid or erythorbic acid is readily oxidized in water, the bicomponental system cannot be preferred as a solvent for the reaction.

As a result of the investigation of organic solvents for the synthesis of the organic ester, it has been found that the reaction proceeds with a good efficiency when the solvent whose solubility (wt/vol) of ascorbic acid or erythorbic acid at 25° C. is 0.3% or more, is used. Among numerous groups of solvents, pyridine (solubility: more than 6%), t-butanol (solubility: 0.62%), dioxane (solubility: 0.57%) or tetrahydrofuran (solubility: 1.1%) is more preferred.

The water content in the reaction system is important to suppress the reverse reaction as described above. It is considered that water bound to the enzyme is necessary to maintain the three-dimensional structure of an enzyme and to keep the enzymatic activity in an organic solvent. A water content is preferably from 100 to 10,000 ppm, more preferably from 1,000 to 5,000 ppm in the organic solvent. A water content higher than 10,000 ppm or lower than 100 ppm will result in an undesirable decrease of the reaction rate and/or increase of the side reactions, such as a reverse reaction and a hydrolysis of enol ester.

The lipase used in the present invention includes any lipase produced by an animal, a plant or a microorganism as long as it has a catalytic activity for the transesterification (ester exchange) reaction of ascorbic acid or erythorbic acid with an organic acid enol ester, and commercially available lipase may be used irrespective of its origin.

When a lipase was deactivated, the lipase can be reactivated by the steps as follows:

(1) Dissolve a deactivated lipase in a buffer, and then concentrate to dryness, (2) Dissolve a deactivated lipase in a buffer, add a surface active agent into the buffer solution and then concentrate to dryness, (3) Dissolve a deactivated lipase in a buffer and then add a diatomaceous earth into the buffer solution to immobilize the lipase on the diatomaceous earth and concentrate to dryness, or (4) Dissolve a deactivated lipase in a buffer, add the surface active agent and diatomaceous earth at the same time into the buffer solution and concentrate to dryness. (A phosphate buffer and lecithin may preferably used as the buffer and surface active agent, respectively.)

Crude lipase or purified lipase may be used, and cells or homogenized cells containing lipase may also be used as a lipase source.

The immobilization of a lipase with a carrier insoluble in the organic solvent noticeably increases the reaction yield.

The carrier includes such inorganic carriers as diatomaceous earth, porous glass, pumice stone, pieces of biscuit and active carbon, and such organic carriers insoluble in the organic solvent as polyethylene resin, polypropylene resin, ion exchange resin, and cross-linked polyacrylamide resin. Among them, porous materials with a large surface area are particularly preferred. A method of ionic bonding to the carrier surface and a method of covalent bonding to the carrier surface chemically treated to introduce, for example, aldehyde groups and isocyanate groups are used for the immobilization of enzyme. Further, since a lipase is usually insoluble in an organic solvent, it can be sufficiently immobilized by a simple and stable method in which a carrier is added into an aqueous solution of a lipase, then they are mixed together with stirring and concentrated to dryness.

A use of a surface active agent for the immobilization is advantageous to improve the stability of the lipase in the organic solvent. The surface active agent is added to the solution of a lipase to make a micelle around the lipase. The immobilization of micelled-lipase thus obtained keeps the organic solvent out of the lipase and protects its enzymatic activity from degradation. The surface active agent used for the immobilization of lipase may be a cationic surface active agent, ampholytic surface active agent or nonionic surface active agent, because the surface of the lipase is anionic. The examples of the cationic surface active agent include an aliphatic ammonium salt and benzalkonium salt. The ampholytic surface active agent includes lecithin (phosphatidyl choline), phosphatidyl serine, phosphatidyl ethanolamine, a carboxybetaine type ampholytic surface active agent, an aminocarboxylate and imidazolinium betaine. In addition, the nonionic surface active agent includes sucrose fatty acid ester, sorbitan fatty acid ester, propylene glycol fatty acid ester, glycerol fatty acid ester, polyethylene glycol fatty acid ester, mannitol dialkylether, sorbitol dialkylether and glycerine monoalkylether.

The transesterification reaction may be carried out in such a way that an organic solvent is added to a mixture of an active lipase or immobilized lipase, ascorbic acid or erythorbic acid, and an organic acid enol ester to get a suspension and then a preferred amount of water is added to the suspension, and thereafter, the suspension is stirred. Gradual flowing of a reaction mixture into a column filled with an immobilized lipase or microorganisms containing an lipase may be used for the transesterification. The reaction temperature is from 10° C. to 90° C., preferably 20° C. to 60° C. The product may be separated from the reaction mixture by a conventional method; for example, separated, washed with water and purified by extraction with an organic solvent.

The present invention provides a process for producing an organic acid ester of ascorbic acid or erythobic acid under milder conditions than those of the conventional processes. The reaction of the present invention may be carried out in an ordinary vessel and purification of the product is greatly facilitated.

EXAMPLES

Now the present invention will be described in further detail with reference to Examples. However, it should be understood that the present invention is by no means restricted by such specific Examples.

Example 1

First, 0.4 g of "Amano Lipase PS" (produced by Amano Seiyaku K.K.) was dissolved in 10 ml of a 1/20 M aqueous phosphate buffer with a pH value of 7, and the solution was then evaporated to dryness under a reduced pressure to obtain a pretreated Lipase PS. Two grams of ascorbic acid and 6.7 g of stearic acid vinylester were dissolved in 40 ml of dried pyridine (water content: 1200 ppm) and the pretreated Lipase PS was added to the mixture. The reaction was carried out at 40° C. with vigorous stirring. Four hours later, the concentration of ascorbic acid-6-stearate in the reaction mixture was found to be 11.5% according to the HPLC (high performance liquid chromatography) analysis. The reaction mixture was filtered and the filtrate was then poured into 200 ml of ice-cooled 6N aqueous hydrochloric acid. The precipitate was filtered, washed with water and then dried under a reduced pressure, whereby 6 g of a crude product was obtained. The crude product was then washed with hot hexane to obtain 5.2 g of a white yellowish product. The content of ascorbic acid-6-stearate in the product was 96%.

Example 2

First, 0.4 g of the "Amano Lipase PS" was dissolved in 10 ml of a 1/20M aqueous phosphate buffer with a pH value of 7 and 3.6 g of diatomaceous earth was added thereto. The mixture was evaporated to dryness under a reduced pressure to obtain an immobilized Lipase PS. Four grams of ascorbic acid and 10.5 g of stearic acid vinylester were dissolved in 40 ml of dried t-butanol (water content: 2000 ppm), and the immobilized Lipase PS was added. The reaction was carried out at 40° C. with vigorous agitation. Twenty-four hours later, the concentration of ascorbic acid-6-stearate in the reaction mixture was found to be 22.2% according to the HPLC analysis. The reaction mixture was filtered and then the filtrate was poured into water. The precipitate was filtered and dried under a reduced pressure, whereby 17.1 g of a crude product was obtained. This was washed with hot hexane to obtain 7.17 g of a refined product. The content of ascorbic acid-6-stearate in the refined product was 95.1%.

Example 3

An immobilized Lipase PS was prepared by the same procedure as in Example 2. Four grams of ascorbic acid and 10.5 g of stearic acid vinylester were dissolved in 40 ml of dried tetrahydrofuran and 4 g of the immobilized Lipase PS was added. The reaction was carried out at 40° C. with vigorous stirring. Twenty-four hours later, the concentration of ascorbic acid-6-stearate in the reaction mixture was found to be 15.3% according to the HPLC analysis. The water content of the reaction system was 1000 ppm.

Example 4

An immobilized Lipase PS was prepared by the same procedure as in Example 2. Two grams of ascorbic acid and 7 g of stearic acid vinylester were dissolved in 40 ml of dried dioxane and 4 g of the immobilized Lipase PS was added. The reaction was carried out at 40° C. Twenty-four hours later, the concentration of ascorbic acid-6-stearate in the reaction mixture was found to be 14.0% according to the HPLC analysis. The water content of the reaction system was 1200 ppm.

Example 5

Four grams of the immobilized Lipase PS prepared by the same procedure as in Example 2 was added to 40 ml of a t-butanol solution (water content: 120 ppm) containing 4 g of ascorbic acid and 12 g of vinyl palmitate. The reaction was continued for 24 hours at 40° C. The reaction mixture was filtered and concentrated to dryness under a reduced pressure. The crude product was recrystallized from ethyl acetate to yield 9.2 g of ascorbic acid-6-palmitate. The water content of the reaction system was 600 ppm.

Example 6

Four grams of the immobilized Lipase PS prepared by the same procedure as in Example 2 was added to 40 ml of a dry t-butanol solution containing 4 g of ascorbic acid and 3 g of vinyl acetate. The reaction was continued for 20 hours at 50° C. The reaction mixture was filtered and concentrated to yield 4.8 g of a crude ascorbic acid-6-acetate. Recrystallization from acetone-benzene gave a crystal with purity of 93%. The water content of the reaction system was 650 ppm.

Example 7

Four grams of the immobilized Lipase PS prepared by the same procedure as in Example 2 was added to 40 ml of a dry tetrahydrofuran solution containing 4 g of ascorbic acid and 3 g of isopropenyl acetate, and then the reaction was continued for 22 hours at 40° C. The reaction mixture was then filtered, concentrated and recrystallized from acetone-benzene to yield 4.5 g of ascorbic acid-6-acetate. The water content of the reaction system was 700 ppm.

Comparative Example 1

To 40 ml of diisopropyl ether (which is widely used for the enzymatic esterification reaction, and the solubility of ascorbic acid at 25° C. is 0.00011%) containing 2 g of ascorbic acid and 6.7 g of stearic acid vinyl ester, 0.4 g of the Lipase PS pretreated by the same way as described in Example 1 was added. The reaction was continued at 40° C. Twenty-four hours later, the concentration of ascorbic acid-6-stearate was determined to be 0.3% according to the HPLC analysis.

Comparative Example 2

Example 1 was repeated with the exception that hexane (ascorbic acid was not dissolved therein at 25° C.) was used as a solvent, and it was found that no reaction had occurred at 40° C. for 24 hours.

Comparative Example 3

Using the Lipase PS pretreated by the same way as in Example 1, 2 g of ascorbic acid and 6 g of stearic acid were allowed to react in 40 ml of dioxane for 24 hours at 40° C., the reaction mixture was analyzed according to the HPLC analysis. The concentration of ascorbic acid-6-stearate was found to be 1.95%. The water content in the reaction system was 11,000 ppm.

Example 8

The same procedures as those of Example 5 were repeated with the exception that vinyl myristate was used instead of vinyl palmitate, and 8.9 g of ascorbic acid-6-myristate was obtained.

Example 9

The same procedures as those of Example 5 were repeated with the exception that erythorbic acid was used instead of ascorbic acid, and 9.1 g of erythorbic acid-6-stearate was obtained.

Examples 10 through 14

(Comparison of stabilization treatments)

One gram of the Amano Lipase PS was dissolved in 25 ml of a 1/20M aqueous phosphate buffer with a pH of 7.0, and 0.8 g of lecithin was added to the buffer solution. After stirring, 10 g of diatomaceous earth was added to the buffer solution and the suspension was further stirred. Subsequently, the suspension was concentrated to dryness under a reduced pressure at 50° C. whereby a stabilized lipase was prepared (Example 10).

On the other hand, 3 kinds of lipases were prepared for comparison of reaction rate using the same procedures as described above except that the lecithin was not added (Example 12), the diatomaceous earth was not added (Example 13), or either the lecithin and the diatomaceous earth were not added (Example 14). Also a commercially available deactivated Lipase PS (not treated by any of the procedures described above) was used (Example 11).

The reactions were carried out in the following way:

To dehydrated t-butanol were added 4 g of ascorbic acid, 4 g of one of the lipases mentioned above (excepting that lipases were added in Examples 12 through 14 in such an amount that the hydrolytic activity were identical to the stabilized lipase in Example 10), and 7.7 g of vinyl stearate, and the reactions were carried out for 24 hours while the temperature of the reaction system was kept at 40° C., respectively, following which the amount of ascorbic-6-acid stearate produced were determined according to the HPLC analysis as shown in Table 1. The water content in the reaction systems were all 400 ppm.

TABLE 1

Amount of Ascorbic Acid-6-Stearate Produced After 24 Hrs of Reaction

| Example No. | Enzyme | Amount of produced ascorbic acid-6-stearate (wt/vol %) |
|---|---|---|
| 10 | Stabilized lipase PS | 20.7% |
| 11 | Commercially available lipase PS | 4.6% |
| 12 | Lipase PS not treated with lecithin | 13.4% |
| 13 | Lipase PS not treated with diatomaceous earth | 17.2% |
| 14 | Lipase PS not treated with either lecithin and diatomaceous earth | 7.5% |

Examples 15 to 17

(Comparison of surface active agents)

Example 10 was repeated with the exception that, sorbitan monostearate, sodium dodecylbenzenesulfonate, or dodecylamine was added instead of lecithin, whereby immobilized lipase were prepared, and reactions were carried out under the same conditions as in Example 10 to obtain the results as shown in Table 2 together with the result of Example 10.

TABLE 2

Comparison of Surface Active Agents

| Example No. | Surface Active Agent | Amount of produced ascorbic acid-6-stearate after 24 hr. (wt/vol %) |
|---|---|---|
| 10 | Lipase PS treated with lecithin (ampholytic surface active agent) | 20.7% |
| 15 | Lipase PS treated with sorbitan monostearate (nonionic surface active agent) | 16.3% |
| 16 | Lipase PS treated with dodecylamine (cationic surface active agent) | 15.9% |
| 17 | Lipase PS treated with sodium dodecylbenzenesulfate (anionic surface active agent) | 3.1% |

Example 18

(Synthesis of ascorbic acid palmitate)

Using the stabilized lipase prepared by the same method as in Example 10, a reaction was carried out for 24 hours under the same conditions as in Example 10 except that 7.4 g of vinyl palmitate was used instead of vinyl stearate. It was found by the HPLC analysis that the concentration of of ascorbic acid-6-palmitate was 19.6%. The water content in the reaction systems was 400 ppm.

Example 19

(Synthesis of ascorbic acid-6-acetate)

Using the stabilized lipase prepared by the same method as in Example 10, a reaction was carried out for 24 hours under the same conditions as in Example 10 except that 2.6 g of isopropenyl acetate was used instead of vinyl stearate. The concentration of ascorbic acid-6-acetate produced in the reaction mixture was found to be 12% by the HPLC analysis.

Example 20

A stabilized lipase was prepared by the same method as in Example 10 with exception that Amano Lipase M10 (produced by Amano Seiyaku K.K.) was used instead of Amano Lipase PS. The stabilized lipase was reacted with vinyl palmitate under the same conditions as In Example 18. Twenty-four hours later, it was found that the concentration of ascorbic acid-6-palmitate was 5.3% by the HPLC analysis.

Example 21

A stabilized lipase was prepared by the same method as in Example 10 with exception that Amano Lipase F (produced by Amano Seiyaku K.K.) was used instead of Amano Lipase PS. The stabilized lipase was reacted with vinyl palmitate under the same conditions as in Example 18. Twenty-four hours later, it was found that the concentration of ascorbic acid-6-palmitate was 5.5% by the HPLC analysis.

Example 22

A stabilized lipase was prepared by the same method as in Example 10 with exception that Amano Lipase AP10 (produced by Amano Seiyaku K.K.) was used instead of Amano Lipase PS. The stabilized lipase was reacted with vinyl palmitate under the same conditions as in Example 18. Twenty-four hours later, it was found by the HPLC analysis that the concentration of ascorbic acid-6-palmitate was 9.3%.

Example 23

A stabilized lipase was prepared by the same method as in Example 10 with exception that Amano Lipase AP6 (produced by Amano Seiyaku K.K.) was used instead of Amano Lipase PS. The stabilized lipase was reacted with vinyl palmitate under the same conditions as in Example 18. Twenty-four hours later, it was found that the concentration of ascorbic acid-6-palmitate was 7.4% by the HPLC analysis.

Example 24

A stabilized lipase was prepared by the same method as in Example 10 with exception that Lipozyme IM20 (produced by Novo Industri A/S, a lipase immobilized to an ion-exchange resin) was used instead of Amano Lipase PS. The stabilized lipase was reacted with vinyl palmitate under the same conditions as in Example 18. Twenty-four hours later, it was found that the concentration of ascorbic acid-6-palmitate was 12.1% by the HPLC analysis.

From the above, it is understood that the amount of the produced organic acid ester of ascorbic acid or erythorbic acid per unit weight of lipase according to the present invention is very high and the reaction selectivity is also high in such an extent that the organic acid ester in the reaction mixture can be isolated and purified much easier than that prepared by the conventional processes.

We claim:

1. A process for producing an organic acid ester, which comprises:

a) reacting ascorbic acid or erythorbic acid with an organic acid enol ester having the formula (1):

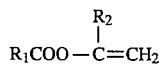

(I)

wherein $R_1$ is a $C_{12}$–$C_{16}$ alkyl group; and $R_2$ is a hydrogen atom or methyl group, in an organic solvent with a solubility (wt/vol) of ascorbic acid or erythorbic acid of 0.3% or more at 25° C. with a lipase immobilized with lecithin and diatomaceous earth to form an organic acid ester of ascorbic acid or erythorbic acid having the formula (II) or (III):

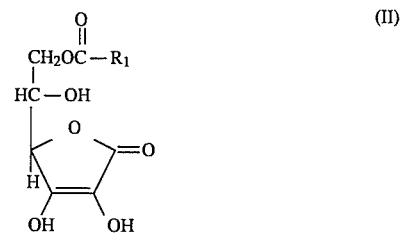

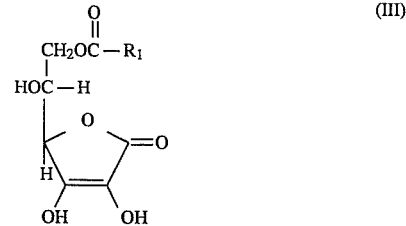

wherein $R_1$ has the same meaning as defined above; and b) recovering the organic acid ester having the formula (II) or (III).

2. The process according to claim 1, wherein the organic solvent is a solvent selected from the group consisting of pyridine, t-butanol, dioxane and tetrahydrofuran.

3. The process according to claim 1 wherein the organic solvent contains from 100 to 10,000 ppm of water.

4. The process according to claim 3, wherein said organic solvent has a water content of from about 1,000 to about 5,000 ppm.

5. The process according to claim 1, which is conducted at a temperature of from about 10° C. to 90° C.

6. The process according to claim 1, which is conducted at a temperature of from about 20° C. to 60° C.

* * * * *